United States Patent [19]

Bailey, III et al.

[11] Patent Number: 4,897,492

[45] Date of Patent: Jan. 30, 1990

[54] METHOD OF PREPARING LOW COLOR FATTY AMIDES

[75] Inventors: Bruce R. Bailey, III; James M. Richmond, both of Naperville, Ill.

[73] Assignee: Akzo America Inc., New York, N.Y.

[21] Appl. No.: 153,861

[22] Filed: Feb. 9, 1988

[51] Int. Cl.[4] .......................................... C07D 233/04
[52] U.S. Cl. ............................................... 548/352
[58] Field of Search .......................................... 548/352

[56] References Cited

U.S. PATENT DOCUMENTS

| | | | |
|---|---|---|---|
| 2,259,968 | 10/1941 | Anderson | 260/420 |
| 2,828,320 | 3/1958 | Gibson | 260/398.5 |
| 3,146,267 | 8/1964 | Weinstein | 548/352 |
| 3,991,056 | 11/1976 | Okamoto et al. | 548/352 |
| 4,189,593 | 2/1980 | Wechsler | 548/352 |
| 4,212,983 | 7/1980 | Phillips et al. | 548/352 |
| 4,216,334 | 8/1980 | Jones | 548/352 |

FOREIGN PATENT DOCUMENTS 0551046  12/1957  Canada ................................ 548/352

*Primary Examiner*—Patrick P. Garvin
*Assistant Examiner*—E. D. Irzinski
*Attorney, Agent, or Firm*—David H. Vickrey; Louis A. Morris

[57] ABSTRACT

Fatty acid amides (such as ditallow amidoethyl imidayoline are prepared by reacting a fatty acid (such as tallow acid) with an amine, particularly an alkyl polyamine (such as diethylene triamine). The products are rendered low in color by the addition of hypophosphorous acid and a hindered phenol compound.

8 Claims, No Drawings

METHOD OF PREPARING LOW COLOR FATTY AMIDES

BACKGROUND OF THE INVENTION

This invention relates to the manufacture of fatty acid amides from fatty acids and amines, particularly alkyl polyamines. In particular, it relates to such methods which yield fatty acid amides with relatively low color.

Fatty amides made from a fatty acid and an amine (particularly an alkyl polyamine) have utility as fabric softeners. Fatty materials in general, fatty amides being no exception, are prone to developing undesirable color upon chemical reaction, heating, and storage. However, consumer uses for fatty amides such as fabric softeners require low color, and high color fatty amides are not saleable in such applications.

One approach to decoloring fatty materials in general is to recrystallize the product. This however, causes product loss and is otherwise expensive. Another approach is to distill the colored product. This is again expensive, and can result in additional color formation if heat is used in the distillation. Yet another approach is the use of liquefied hydrocarbon gases such as propane to extract colored components. This last approach, however, is both expensive and poses an additional safety hazard because of the flammable or explosive nature of such gases. One problem unaddressed by these solutions is that after decolorization, the fatty materials will tend to become colored during storage.

U.S. Pat. No. 2,828,320 (Gibson-Swift & Co., 1958) teaches stabilization of the color of previously decolorized fatty acids with a blend of hypophosphorous acid and one of di-tertiarybutyl para cresol (BHT), butylated hydroxy anisol, beta napthol, propyl gallate, or hydroquinone. This patent does not, however, address the problem of color formation during reaction and does not address the possible reaction of the stabilizer materials with the intended reactants.

Japanese publication 35528/1970 (Fuchizawa-Japan Ushi (Oil and Fat) Co., 1970) specifically addresses the production of fatty acid bisamides, and uses a mixture of (1) a phosphorous acid, a hypophosphorous acid, or an alkali or alkyline earth salt thereof, and (2) an alkali borohydride. This process, however, does not stabilize the color of the product as much as would be desired.

DETAILED DESCRIPTION OF THE INVENTION

In this specification and claims, numerical ranges are not critical unless otherwise stated. That is, the numerical ranges may be read as if they were prefaced with the word "about" or "substantially".

A first component of the invention is a $C_4$ to $C_{22}$ carboxylic acid. Such acids are commonly referred to as fatty acids and are typically derived from natural sources such as pressed plant oils and slaughter house scrap. Because of their natural origin, such acids will usually be a mixture of similar acids rather than a single species. These fatty acids may be either saturated or unsaturated. If in its "natural" form an acid is unsaturated, it may be partially or completely hydrogenated to reduce or eliminate unsaturation. For purposes of this invention, by "fatty acid" is also meant esters of the acid. In particular, triglicerides of fatty acids are convenient because of their ready availability from animal sources. If triglicerides are used, glicerine, rather than water, will be removed during the reaction. Of the $C_4$ to $C_{22}$ acids, $C_6$ to $C_{22}$ acids are desired, and $C_8$ to $C_{22}$ are more desired. Preferred acids are $C_{12}$ to $C_{18}$ acids such as tallow acid and hydrogenated tallow acid.

A second component of the invention is an an amine. Suitable amines include simple monoamines such as ethyleneamine, fatty monoamines such as tallowamine, and alkyl polyamines. In a preferred embodiment of the invention the amine is an alkyl polyamine of the formula $$NH_2(CH_2)_m[NH(CH_2)_m]_pNH_2,$$

wherein each m is independently from 2 to 8 and p is from 0 to 3. Although it is not required, it is preferred that the triamine be symmetrical (i.e.: that all values of m are the same. It is preferred that $p=0$ or 1 and most preferred that $p=1$. Diethylenetriamine ($m=2$ and $p=1$) is most preferred and each higher analog ($m=3$ to 8) is succeedingly less preferred because of lower reactivity in the reaction of the invention.

A third component of the invention is hypophosphorous acid ($H_3PO_2$), including salts thereof. If salts are used, it is preferred that they be alkali or alkaline earth salts. Sodium and potassium are preferred counter ions. More preferred than the salts is the acid itself. Hypophosphorous acid is typically sold in 30–50% aqueous solutions and may be used as such.

A fourth component of the invention is a hindered phenol compound. By "hindered phenol compound" is meant an aromatic compound having a hydroxyl group attached directly to the aromatic ring, and at least one moiety ortho the phenol which causes steric hindrance. To be considered a hindered phenol a compound must function as an antioxidant by abstraction of free radicals. Preferred hindered phenol compounds have the formula

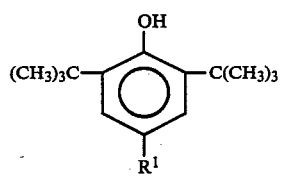

wherein $R^1$ is optional and if present is an organic moiety such as lower alkyl (methyl, ethyl, etc) or a polymeric materials. It is preferred that $R^1$ be of relatively high molecular weight because higher molecular weight hindered phenols have been found to be more effective in the invention.

Examples of suitable hindered phenols include butylated hydroxytoluene (BHT) (2,6-di-tert-butyl-para-cresol), butylated hydroxyanisole (BHA) (a mixture of 2- and 3-tert-butyl-4-methoxy phenol), and higher molecular weight hindered phenols sold under the trademark "IRGANOX" (by Ciba-Geigy Corp.) such as Irganox 1010 and Irganox 1076.

The fatty acid is reacted with the amine (preferably polyamine) using (except for the addition of the hypophosphorous acid and the hindered phenol) conventional techniques and conditions. The fatty acid and amine are used in a molar ratio with a slight (e.g.: about 1%) excess of amine preferred to allow for loss in the reaction apparatus. Typically, the fatty acid, hypophosphorous acid, and hindered phenol will be charged to a reactor which will then be purged with nitrogen to remove all oxygen. The amine will then be added, the pressure reduced to 3 to 50 kPa (absolute) (preferably 3 to 7 kPa), and the reaction mixture heated to 160° to 250° C., preferably 180° to 225° C. for 0.5 to 50, preferably 1 to 20, more preferably 1 to 4 hours. The use of a solvent is not necessary but may be used to assist with removal of the product from the reactor. Reduced pressure during the reaction is greatly preferred for removal of water of reaction and significantly reduces the reaction time. A nitrogen flow of about 0.005 m³/hr/kg of reactant is useful for ensuring lack of oxygen entry and as an aid in removing waters of reaction. The process of the invention is very sensitive to minor variations in the procedure. One of the most critical factors is the exclusion of oxygen from the system. Allowing even minor amounts of oxygen to enter the reaction vessel will cause significant color. Thus, it is preferred that all possible measures be taken excluded oxygen. Elevated temperature is greatly preferred for complete reaction. In the preferred embodiment wherein the amine is diethylenetriamine, the product is a diakylamidoethylimidazoline of the formula

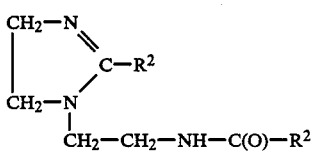

wherein each $R^2$ represents the residue of the particular fatty acid used in the reaction.

The hypophosphorous acid and the hindered phenol compound are each present in a synergistic mixture. By "synergistic mixture" is meant that each is present, relative to the other, in an amount such that the mixture is more effective at reducing color in the product than an equivalent weight of either component alone. Further, the hypophosphorous acid and the hindered phenol compound are used together in a color stabilizing amount. By "color stabilizing amount" is meant an amount of the mixture, in relation to the reactants and product, which is sufficient to render the product less colored than if the hypophsophorous acid and hindered phenol compound were not present.

Following the above requirements, the hypophosphorous acid is desirably at 0.005 to 0.5, more desirably 0.01 to 0.25, and preferably 0.05 to 0.1 weight percent, based on the weight of the total reaction charge. The hindered phenol is desirably present at 0.001 to 5.0, more desirably 0.01 to 3.0, and preferably 0.1 to 1.0 weight percent, based on the weight of the total reaction charge.

The color of the amides produced by the process of the invention is very low, and remains relatively low during storage. The storage stability can be further increased by a post-reaction addition of the hindered phenol, but such post reaction addition is not as important when the preferred high molecular weight hindered phenols are used in the initial reactor charge. If a post treatment is used it is used in a post treatment color stabilizing amount. By "post treatment color color stabilizing amount" is meant an amount of the hindered phenol which, when added subsequent to the reaction, will render the amide more color stable than if it were not added. The hindered phenol is thusly present (as a post treatment) in an amount of 0.005 to 0.5, more desirably 0.01 to 0.25, and preferably 0.05 to 0.1 weight percent, based on the weight of the total reaction charge.

The invention will be further illustrated by the following examples. In the examples, all parts and percentages are by weight unless otherwise specified.

THEORECTICAL EXAMPLE 1

A reaction vessel is fitted with a vacuum source and a nitrogen source. The vessel is charged with 1 equivalent tallow acid, 0.1% BHT, and 0.1% of a 50% aqueous solution of hypophosphorous acid (both percents based on fatty acid plus polyamine). The vessel is flushed with nitrogen to remove all oxgyen and 1 equivalent diethylene triamine is added. The vessel is heated to 180° to 225° C. under vacuum with a nitrogen flow. After 2 hours the product shows a high degree of ring closure and a very low Gardner color value. Upon storage for 14 days at 90° C. the color value has risen. A similar sample treated with 0.1% BHT after the reaction continues to have a very low color value after similar storage at elevated temperature.

We claim:

1. A method of preparing a fatty acid amide comprising reacting together a $C_4$ to $C_{22}$ carboxylic acid and an amine, characterized in that the reaction is carried out in the presence of a color stabilizing amount of a synergistic mixture of hypophosphorous acid and a hindered phenol compound.

2. A method of preparing a fatty acid amide comprising reacting together a $C_4$ to $C_{22}$ carboxylic acid and an alkyl polyamine of the formula

$$NH_2(CH_2)_m[NH(CH_2)_m]_pNH_2$$

wherein each m is independently from 2 to 8 and p is from 0 to 3 characterized in that the reaction is carried out in the presence of a color stabilizing amount of a synergistic mixture of hypophosphorous acid and a hindered phenol compound.

3. The method of claim 1 wherein the alkyl polyamine is a dialkyl triamine.

4. The method of claim 2 wherein the hypophosphorous acid is present at 0.005 to 0.5 percent, based on the weight of the fatty acid and the polyamine.

5. The method of claim 3 wherein the hypophosphorous acid is present at 0.05 to 0.1 percent, based on the weight of the fatty acid and the polyamine.

6. The method of claim 2 wherein the hindered phenol compound is present at 0.001 to 5.0 percent, based on the weight of the fatty acid and the polyamine.

7. The method of claim 5 wherein the hindered phenol compound is present at 0.1 to 1.0 percent, based on the weight of the fatty acid and the polyamine.

8. A fatty amide prepared by the method of claim 1.

* * * * *